US008552364B2

(12) United States Patent
Graves et al.

(10) Patent No.: US 8,552,364 B2
(45) Date of Patent: Oct. 8, 2013

(54) SERUM PROTEOMICS SYSTEM AND ASSOCIATED METHODS

(75) Inventors: Steven W. Graves, Highland, UT (US); Craig Dan Thulin, Lindon, UT (US); Michael Sean Esplin, Salt Lake City, UT (US)

(73) Assignees: Brigham Young University, Provo, UT (US); University of Utah Research Foundation, Salt Lake City, UT (US); IHC Health Services, Salt Lake City, UT (US)

( * ) Notice: Subject to any disclaimer, the term of this patent is extended or adjusted under 35 U.S.C. 154(b) by 454 days.

(21) Appl. No.: 12/521,027

(22) PCT Filed: Dec. 26, 2007

(86) PCT No.: PCT/US2007/026346
§ 371 (c)(1),
(2), (4) Date: Mar. 16, 2010

(87) PCT Pub. No.: WO2008/079407
PCT Pub. Date: Jul. 3, 2008

(65) Prior Publication Data
US 2010/0163721 A1    Jul. 1, 2010

Related U.S. Application Data

(60) Provisional application No. 60/877,209, filed on Dec. 26, 2006.

(51) Int. Cl.
*H01J 49/00* (2006.01)
(52) U.S. Cl.
USPC .......................................... 250/282; 250/281
(58) Field of Classification Search
USPC ......... 250/281, 282, 283, 284, 287, 288, 299, 250/300; 435/23, 24
See application file for complete search history.

(56) References Cited

U.S. PATENT DOCUMENTS 7,300,753 B2 * 11/2007 Rush et al. .................. 435/7.23
7,446,312 B2 * 11/2008 Rather ......................... 250/288
(Continued)

FOREIGN PATENT DOCUMENTS

WO          0122078        3/2001
WO        2006110848      10/2006

OTHER PUBLICATIONS

International Preliminary Report on Patentability dated Jul. 9, 2009 for international application No. PCT/US07/026346.
(Continued)

*Primary Examiner* — Robert Kim
*Assistant Examiner* — Jason McCormack
(74) *Attorney, Agent, or Firm* — Gardner Groff Greenwald & Villanueva, P.C.

(57) ABSTRACT

Methods for proteomic analysis are provided. For example, in one aspect a method for identifying and sequencing a peptide may include fractionating a biological sample containing a peptide of interest to at least partially isolate the peptide, obtaining mass spectra of the peptide, and accelerating the peptide into a collision chamber at a plurality of discrete collision energies for a discrete period of time to form a plurality of peptide fragments for each of the plurality of discrete collision energies. The method may further include obtaining a plurality of fragmentation mass spectra from the plurality of peptide fragments for each of the plurality of discrete collision energies, summing the plurality of fragmentation mass spectra from each of the plurality of discrete collision energies to form a plurality of discrete collision energy mass spectra, one discrete collision energy mass spectra from each discrete collision energy, summing the plurality of discrete collision energy mass spectra to form a final mass spectrum for the peptide fragments, and identifying a sequence of amino acids corresponding to the peptide from the final mass spectrum.

18 Claims, 5 Drawing Sheets

(56) References Cited

U.S. PATENT DOCUMENTS

| | | | |
|---|---|---|---|
| 2002/0137106 A1* | 9/2002 | Leung et al. .................... | 435/7.9 |
| 2002/0182649 A1* | 12/2002 | Weinberger et al. ........... | 435/7.9 |
| 2003/0119063 A1* | 6/2003 | Pham ............................ | 435/7.1 |
| 2005/0092910 A1* | 5/2005 | Geromanos et al. ........... | 250/282 |
| 2005/0167582 A1* | 8/2005 | Zavitsanos et al. ............ | 250/282 |
| 2005/0260697 A1* | 11/2005 | Wang et al. ..................... | 435/23 |
| 2006/0043285 A1* | 3/2006 | Laskin et al. .................. | 250/288 |
| 2006/0121473 A1* | 6/2006 | Tanga et al. ......................... | 435/6 |
| 2006/0255259 A1* | 11/2006 | Zubarev et al. ............... | 250/282 |
| 2007/0031911 A1* | 2/2007 | Leite et al. ....................... | 435/23 |
| 2007/0054345 A1* | 3/2007 | Hunter ............................ | 435/23 |
| 2007/0114375 A1* | 5/2007 | Pevsner et al. ................. | 250/282 |
| 2008/0142696 A1* | 6/2008 | Geromanos et al. ........... | 250/282 |
| 2009/0042229 A1* | 2/2009 | Folkman et al. ................ | 435/23 |

OTHER PUBLICATIONS

European Search Report dated Aug. 16, 2010 for international application No. EP07863251.0-2404/2118652.

Kayganich et al. "Comparison of tandem and conventional mass spectrometry using electron capture negative ionization in the detection of chemically oxidized dexamethasone in human plasma", Journal of the American Society for Mass Spectrometry, Elsevier Science Inc, US LNKD, vol. 1, No. 4, Jul. 1990, pp. 341-348.

Wan et al. "Quantitative analysis of [Dmt<1>]DALDA in ovine plasma by capillary liquid chromatography-nanospray ion-trap mass spectrometry", Journal of Chromatography B: Biomedical Sciences & Applications, Elsevier, Amsterdam, NL LNKD, vol. 803, No. 1, Apr. 2004, pp. 83-90.

Williams et al. "Sub Parts-Per-Million Mass Measurement Accuracy of Intact Proteins and Product Ions Achieved Using a Dual Electrospray Ionization Quadruple Fourier Transform Ion Cyclotron Resonance Mass Spectrometer", Journal of the American Society for Mass Spectrometry, Elsevier Science Inc, US LNKD, vol. 18, No. 1, Sep. 2006, pp. 1-7.

Response to European Search Report dated Jun. 22, 2011.

Miura, "Novel Human Plasma Proteins, HRP (Acute Phase Protein) and PHPB (Serine Protease), Which Bind to Glycosaminoglycans", Curr. Med. Chem.—Cardiovascular & Hematological Agents, 2004, vol. 2, No. 3, pp. 239-248, Bentham Science Publishers Ltd., Japan.

Miura et al., "The novel acute phase protein, IHRP, inhibits actin polymerization and phagocytosis of polymorphonuclear cells", Inflammation Research, 2000, vol. 49, pp. 305-310, Birkhasuser Verlag, Basel, Japan.

Daveau et al. "Hepatic and Extra-hepatic Transcription of Inter-a-inhibitor Family Genes under Normal of Acute Inflammatory Conditions in Rat", Archives of Biochemistry and Biophysics, 1998, vol. 350, No. 2, pp. 315-323, Academic Press.

Dugoff et al. "Quad Screen as a Predictor of Adverse Pregnancy Outcome", Obstetrics & Gynecology, 2005, vol. 16, No. 2, pp. 260-267, American College of Obstetricians and Gynecologists.

Nishimura et al. "cDNA and deduced amino acid sequence of human PK-120, a plasma kallikrein-sensitive glycoprotein", FEBS Lett 1995 357:207-211.

Pineiro M. "ITIH4 (Inter-Alpha-Trypsin Inhibitor Heavy Chain 4) Is a New Acute-Phase Protein Isolated from Cattle during Experimental Infection", Infect Immun 2004;72:3777-3782.

Zhang Z et al. "Three Biomarkers Identified from Serum Proteomic Analysis for the Detection of Early Stage Ovarian Cancer", Cancer Res 2004;64:5882-5890.

Soury et al. "The H4P Heavy Chain of Inter-a-inhibitor Family Largely Differs in the Structure and Synthesis of Its Prolin-Rich Region from Rat to Human", Biochem Biophys Res Commun 1998 243:522-530.

Swamy GK et al. "Clinical utility of fetal fibronectin for predicting preterm birth", J Reproductive Med 2005;50:851-856.

* cited by examiner

SERUM PROTEOMICS SYSTEM AND ASSOCIATED METHODS

PRIORITY DATA

This application claims the benefit of U.S. Provisional Patent Application Ser. No. 60/877,209, filed on Dec. 26, 2006, which is incorporated herein by reference in its entirety.

FIELD OF THE INVENTION

The present invention relates to isolating and identifying peptides from biological samples. Accordingly, this invention involves the fields of biotechnology, chemistry, and other health sciences.

BACKGROUND OF THE INVENTION

Proteomics relates to the large scale study of proteins, with a particular focus in many cases on structure and function. Proteins have proven challenging to study, particularly on such a large scale. Such difficulties are due, in part, to, the high variability in the expression of proteins between cells of different types, as well as between cells of the same type experiencing differential biological interactions. Additionally, a large number of proteins can be expressed from a single gene due to alternative splicing or post translational modifications. It has been estimated that greater than 500,000 proteins are expressed in humans from the approximately 25,000 coding genes in the human genome. Given such enormous numbers of proteins that may be present in a biological sample, studying single peptides or proteins either within a single sample or across a number of samples is a difficult task.

One aspect of proteomics that is particularly difficult pertains to the locating and sequencing of a peptide that is present in a subject due to a medical or other condition that may not be present in the general population or present in significantly altered concentration. Such peptides may also occur at very low quantities in the biological sample, thus further increasing the difficulty of peptide identification. The complexity of this search is further exacerbated because the peptide is often unknown, and thus a search is performed for any peptide differences between the biological sample from the subject of interest and biological samples from a control group in an attempt to find those factors that may mediate, diagnose or predict the condition. Once found, however, such peptide differences may lead to diagnostic or prognostic tests for a particular condition or even subsequent medical treatment to minimize or eliminate the condition or the effects of the condition.

SUMMARY OF THE INVENTION

Accordingly, the present invention provides proteomic systems and methods. In one aspect, for example, a method for comparing multiple mass spectra from different biological samples, locating mass ions that are quantitatively different after using approaches to compensate for non-biological variability, and isolating and sequencing at least one peptide of interest thus allowing for identification of the peptide from a biological sample, is provided. Such a method may include fractionating each of a plurality of biological samples to form a plurality of elutions, obtaining a plurality of mass spectra from each of the plurality of elutions at a plurality of elution times, and finding a molecular ion peak of interest that appears to be quantitatively different between biological samples. The method may additionally include identifying a mass spectrum reference peak corresponding to an endogenous reference molecule that is substantially consistent between biological samples, the endogenous reference molecule having an elution time and a mass to charge ratio that are substantially similar to the peak of interest, and compensating for non-biological variation for each biological sample across the plurality of elutions by normalizing the peak of interest to a mass spectrum peak of the endogenous reference molecule. The method may further include conducting collision-induced fragmentation studies that use each of a plurality of collision energies one run at a time and summing resulting pluralities of fragment ion mass spectra without averaging to form a single cumulative daughter fragment mass spectrum, and use the daughter fragment mass spectrum to establish amino acid sequence data which is then used in identifying a peptide corresponding to a peak of interest in the single aligned mass spectrum.

In a further aspect of the present invention, the method may also include identifying a plurality of mass spectrum elution time alignment peaks in the plurality of mass spectra corresponding to a plurality of endogenous alignment molecules such that each of the plurality of elutions contains at least one mass spectrum elution time alignment peak, and aligning at least a portion of the plurality of mass spectra by aligning at least a portion of the plurality of mass spectrum elution time alignment peaks.

In one another aspect a method for isolation and identification of a peptide from a biological sample is provided. Such a method may include fractionating each of a plurality of biological samples to form a plurality of elutions, obtaining a plurality of mass spectra from each of the plurality of elutions at a plurality of elution times, and identifying a mass spectrum alignment peak corresponding to an endogenous alignment molecule that elutes in each of the plurality of elutions. The method may further include aligning the pluralities of mass spectra from each elution by aligning the mass spectrum alignment peak from each of the plurality of elutions, summing the pluralities of aligned mass spectra to form a single aligned mass spectrum, and identifying a peptide corresponding to a peak of interest in the single aligned mass spectrum. Although various techniques are contemplated, in one aspect aligning the pluralities of mass spectra may further include visually aligning the pluralities of mass spectra. Additionally, fractionating each of the plurality of biological molecules present in a plurality of biological samples may be accomplished by numerous methods, for example by capillary liquid chromatography (cLC).

In another aspect of the present invention, identifying the peptide corresponding to the peak of interest in the single mass spectrum may further include fractionating at least one of the biological samples containing the peptide associated with the peak of interest to at least partially isolate the peptide, obtaining mass spectra of the peptide, and accelerating the peptide into a collision chamber at a plurality of discrete collision energies for a discrete period of time to form a plurality of peptide fragments for each of the plurality of discrete collision energies. The method may further include obtaining a plurality of fragmentation mass spectra from the plurality of peptide fragments for each of the plurality of discrete collision energies, summing the plurality of fragmentation mass spectra from each of the plurality of discrete collision energies to form a plurality of discrete collision energy mass spectra, one discrete collision energy mass spectra from each discrete collision energy, summing the plurality of discrete collision energy mass spectra to form a final mass spectrum for the peptide, and identifying a sequence of amino acids corresponding to the peptide from the final mass spectrum.

Obtaining fragmentation mass spectra at a plurality of discrete collision energies for a discrete period of time may allow the sequencing and identification of larger peptides than has previously been possible using current techniques. In one aspect, the discrete period of time is approximately equal to the peptide's elution duration, or in other words, the time it takes for the peptide to elute from a cLC column. In another aspect, the discrete period of time is greater than or equal to the peptide's elution duration. In yet another aspect, the discrete period of time is from about 30 seconds to about 3 minutes. Furthermore, non-biological variability between samples and sample runs may detrimentally affect the identification of a peptide. Accordingly, in one aspect, the method may further include identifying a mass spectrum reference peak corresponding to an endogenous reference molecule in proximity to the peak of interest and normalizing the pluralities of mass spectra from each of the plurality of elutions to the mass spectrum reference peak to compensate for non-biological variability between biological samples.

The present invention additionally provides methods for sequencing peptides. In one aspect, for example, such a method may include fractionating a biological sample containing a peptide of interest to at least partially isolate the peptide, obtaining mass spectra of the peptide, and accelerating the peptide into a collision chamber at a plurality of discrete collision energies for a discrete period of time to form a plurality of peptide fragments for each of the plurality of discrete collision energies. The method may further include obtaining a plurality of fragmentation mass spectra from the plurality of peptide fragments for each of the plurality of discrete collision energies, summing the plurality of fragmentation mass spectra from each of the plurality of discrete collision energies to form a plurality of discrete collision energy mass spectra, one discrete collision energy mass spectra from each discrete collision energy, summing the plurality of discrete collision energy mass spectra to form a final mass spectrum for the peptide, and identifying a sequence of amino acids corresponding to the peptide from the final mass spectrum.

DEFINITIONS OF KEY TERMS

Figure 1:
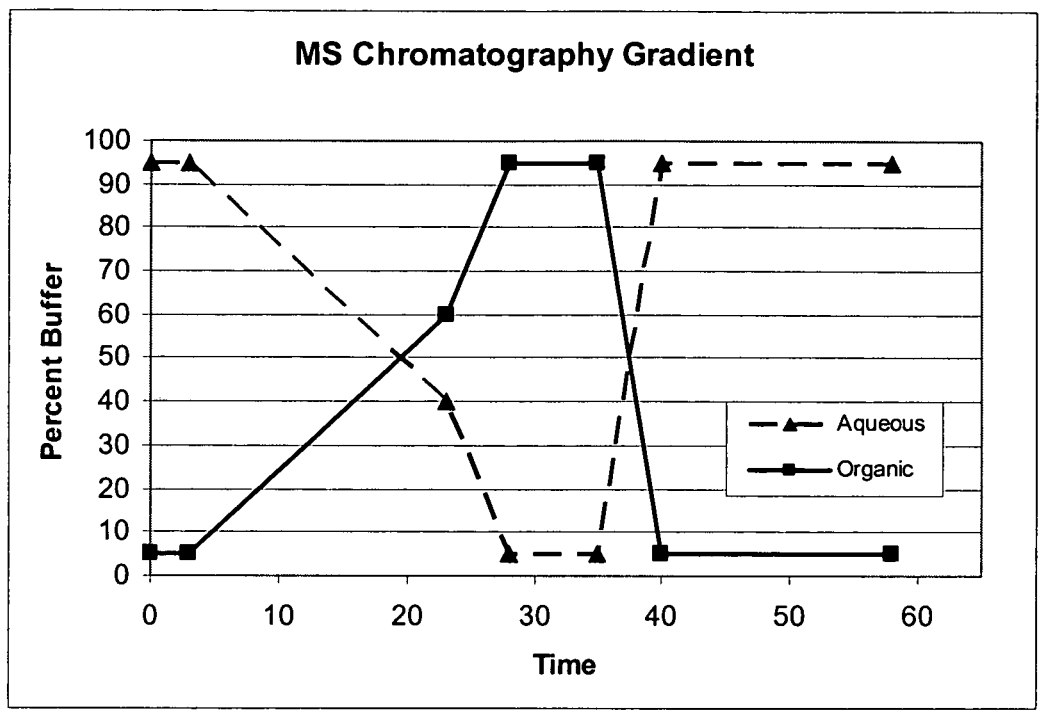
FIG. 1 is a capillary liquid chromatography solvent gradient elution profile in accordance with one embodiment of the present invention.

In describing and claiming the present invention, the following terminology will be used in accordance with the definitions set forth below.

The singular forms "a," "an," and, "the" include plural referents unless the context clearly dictates otherwise. Thus, for example, reference to "a peptide" includes reference to one or more of such peptides, and reference to "an antibody" includes reference to one or more of such antibodies.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals.

As used herein, "biological sample" may be used to refer to any biological material taken from a subject. Such material may include blood serum, whole blood, lymph, urine, saliva, tissue, feces, or any other biological material that may contain peptides.

As used herein, the term "peptide" may be used to refer to a natural or synthetic molecule comprising two or more amino acids linked by the carboxyl group of one amino acid to the alpha amino group of another. A peptide of the present invention is not limited by length, and thus "peptide" can include polypeptides and proteins.

As used herein, the term "isolated," with respect to peptides, refers to material that has been removed from its original environment, if the material is naturally occurring. For example, a naturally-occurring peptide present in a living animal is not isolated, but the same peptide, which is separated from some or all of the coexisting materials in the natural system, is isolated. Such isolated peptide could be part of a composition and still be isolated in that the composition is not part of its natural environment. An "isolated" peptide also includes material that is synthesized or produced by recombinant DNA technology.

As used herein, the term "non-biological variation" refers to any detectable variation in mass spectra between biological samples that is of a non-biological nature. As examples, such variation may include variation due to storage of the samples, pre-cLC processing, cLC processing, MS processing, etc.

As used herein, the term "substantially uniform abundance" refers to an abundance of a substance in each of the plurality of samples that generates a substantially uniform mass spectral peak for the substance from each of the plurality of samples.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

DETAILED DESCRIPTION

Aspects of the present invention provide techniques for isolating and identifying peptides from biological samples. Many of the techniques may be utilized to greatly increase the number of peptides screened and isolated from a sample, as well as greatly increasing the size of identified and sequenced peptides. Generally, one aspect of the present invention may include peptide separation, identifying clinically or scientifically relevant quantitative differences in peptide abundance, peptide sequencing and identification. It should be noted that the techniques described herein for separation, isolation, and sequencing of peptide are meant to be merely exemplary, and the scope of the present invention should not be limited thereby.

Peptide separation or fractionating, for example, may be performed by a variety of techniques, and any such separation method would be considered to be within the scope of the present invention. In one aspect, peptide separation may be accomplished via capillary liquid chromatrography (cCL). cLC is a separation technique wherein the mobile phase is a liquid, and separation of peptides occur as a biological sample moves through a packed column. Thus separation occurs due to the differential interactions of peptides in the mixture with the packing material giving rise to different speeds of movement of the peptides through the column. The mobile phase carrying the peptides exits the column as an elution, with peptides eluting from the column at an elution time that is related to the peptide's size or chemical properties, including in some cases its charge distribution. Thus an elution may represent the fractionating of a substantial portion of the entire biological sample, or an elution may represent a discrete time window from which only a portion of the biological sample is fractionated. In some aspects, a biological sample may be fractionated into a plurality of elutions, each having a discrete elution time period.

Additionally, cLC devices utilize very small diameter columns and thus can process relatively small quantities of biological samples. In some cases a relatively high pressure may also be used, a technique referred to as high performance liquid chromatography (HPLC).

Peptide identification may also occur by any method known to one of ordinary skill in the art. In one aspect, for example, the elution from a cLC capillary column may be coupled directly to a mass spectrometer for subsequent analysis and identification. Mass spectrometry (MS) is an analytical technique used to measure the mass-to-charge ratio (m/z) of ionic species. Generally, peptides in the eluate pass through a charged needle and the acidified liquid of the mobile phase is atomized into very fine droplets. The water and other solvents in this mist rapidly evaporate leaving behind charged peptides. Because the peptides have a charge, they can be controlled by an electric or magnetic field. These peptide ions are moved into a mass detector chamber where they are 'pulsed' or caused to move through a slit in a perpendicular direction by a magnet or electrode and into a time-of-flight (TOF) drift tube. The ions receive similar kinetic energy from the pulse and travel with a velocity inversely proportional to their mass, the small ions moving more rapidly. Small differences in kinetic energy are compensated for by an ion mirror in the drift tube and the ions are reflected and travel further to the detector. The time required for an ion to arrive at the detector then provides a highly accurate mass to charge ratio (m/z). The abundance of a given peptide is proportional to the size of the peak recorded by the mass spectrometer's detector for a given m/z. When a peptide is of interest and further characterization is desirable, it is often necessary to couple two mass spectrometers. This is called tandem mass spectrometry or two dimensional or two sector mass spectrometry. This allows for peptide ions of interest, seen in the first dimension to be moved from the first mass spectrometer by means of an electric voltage and accelerated through a chamber containing low levels of inert gas. In this collision chamber the ions randomly collide with the gas producing on average one collision per molecule. The voltage difference determines the rate of acceleration and the energy of the collisions. The collisions preferentially break peptide bonds, producing ion fragments of the parent peptide that are broken between amino acids. The fragments thus produce are moved into a second mass spectrometer. Here they are pulsed into the flight tube of that instrument and their m/z ratio determined. This series of fragments can provide a substantial, even a complete set of ion fragments broken between every amino acid.

The difference in mass between the fragments nearest in molecular weight represents the mass of the missing amino acid. Thus, one can determine amino acid sequence for the parent peptide provided that there is sufficient signal to populate all of the fragments.

One problem that may arise in many proteomic methods relates to analytical variability between biological sample runs. For example, samples that are run on different days or in different columns can vary in elution times. Such variability can affect the informational content gathered from a proteomic method. In order to overcome these problems, it has now been discovered that such variability can be reduced or eliminated through a novel form of peak alignment. For example, in one aspect a number of endogenous reference molecules spaced throughout the elution period may be identified that have a relatively high abundance and are present in all biological samples being tested in a group that elute from a cLC column an approximately periodic interval. An endogenous alignment molecule may be used as a reference point to align the mass spectra by adjusted elution time across a number of elutions, whether they have been run on different days, are from different biological samples, or have been run on different columns. By aligning mass spectra from the several elutions the point of occurrence of a peptide peak is aligned with the same species in other sample elutions, and thus the information content obtained from the mass spectra can be increased because of increasing accuracy.

In some aspects it may also be beneficial to smooth the mass spectra in order to more accurately locate the center of the peak of the endogenous alignment molecule to further increase the accuracy of the alignment process. Such smoothing may be accomplished by any means known, including Gaussian or other filter functions. Once smoothed, the mass spectra may be aligned across elution times as described.

Aligning mass spectra may be accomplished by any technique known, including automated and manually manipulated methods. In one aspect, however, it may be useful to visually align the mass spectra to allow a potentially more accurate correspondence therebetween. In such a visual alignment, software associated with the MS device can create visual images of the mass spectra that can be manually manipulated within the software to allow the overlaying of spectra from the same elution interval from different sample runs. Overlaying the spectra allows visual inspection for differences between samples that may be difficult to replicate with automated processes. Such differences may be indicative of peptides present in one sample but not in others.

One problem that may arise when processing biological samples pertains to occasional non-biological variability between samples. Such variability generally affects all mass spectral peaks within that run of the elution. Thus the overall level of spectral peaks for a given set of peptides may be significantly different from other elution runs. Such variability may be mistakenly taken to be a significant difference between biological samples, and thus obscure actual significant data within the proteomic analysis. To compensate, it has been discovered that non-biological variability can be accounted for by identifying a mass spectrum reference peak corresponding to an endogenous reference molecule in proximity to the peptide peak of interest and normalizing the pluralities of mass spectra within each elution using the mass spectrum reference peak. It is helpful if the endogenous reference molecule has a high and relatively constant abundance across all biological samples to thus allow accurate normalization.

After alignment of elution time and creation of displays of mass spectra representing specimens of two groups, for example representing individuals with a particular medical problem and representing individuals without the medical complication, coded by color, it is possible to inspect the peaks in the different elution intervals to locate peaks that appear to differ quantitatively. In some aspects it may also be beneficial to reduce pre-analytical and analytical variation by the use of mass spectral peaks arising from the specimen analyzed that are not different between groups but close in mass and elution time to the peak of interest that appears quantitatively different. These internal, endogenous controls allow for compensation of pre-analytical and analytical variability by normalizing (rescaling) the peaks that appear quantitatively different to this reference peak. This is possible because most mass spectral peaks are proportionally represented across the entire mass spectrum for a given specimen, for example if one specimen appears less abundantly represented in its mass spectrum in comparison to another, the vast majority of peaks for that specimen will be smaller, except where there are biological changes. Reducing non-biological variability allows for easier and more accurate identification of biologically mediated differences in a peptide's abundance between comparison groups.

Peptides identified as quantitatively different by MS analysis may be further analyzed and sequenced by any methods know to those of ordinary skill in the art. In one aspect, for example, peptides selected for further analysis may be processed via a tandem MS-MS system. The original biological sample may be used to elute the peptide by cLC. The elution can be directly fed into a first MS process that functions as described above to isolate the protein from the remaining cLC elution. The selected peptide is then accelerated into a collision cell where it collides with an inert gas and fragments at peptide bonds as described above. A second MS process then analyzes the daughter fragments from the first MS process and the results are used to provide amino acid sequence information which then allows a search of protein databases for matching sequences.

The fragmentation pattern of a peptide may vary in proportion to the velocity of acceleration of the peptide into the collision cell. Thus by increasing the collision energy of the peptide, peptide bonds that remain unbroken at lower collision energies may break at higher collision energies. Various prior art methods have utilized a linear and continuous increase in collision energy to create a fragmentation pattern for a peptide. Such a linear and continuous increase, however, may not allow adequate time for collection of peptide fragments at any one collision energy if the peptide is not of high abundance. As such, peptide sequencing using such a technique has been limited. A novel sequencing method has now been discovered that greatly increases the size of peptide that can be sequenced and the reliability of the resulting amino acid sequence. Accordingly, in one aspect a peptide is accelerated into a collision chamber at a plurality of discrete collision energies for a discrete period of time, with one collision energy applied for one cLC-MS run. In one aspect, the discrete period of time may be the period of peak elution. By maintaining a constant collision energy for a discrete amount of time, a large number of ions for a series of peptide fragments can be obtained. The specimen is then rerun using a second, third, or many collision energies, thus populating additional fragment ions with much higher ion counts and peak amplitudes, improving subsequent sequencing and identification. Thus a large number of mass spectra fragmentation patterns can then be obtained from the peptide fragments at each discrete collision energy.

Prior techniques have utilized an averaging method of all mass spectra over the peak of interest elution interval to combine the mass spectra fragmentation patterns obtained from the linear and continuous collision energy increase into a single mass spectra pattern. Such a process tends to diminish peak amplitudes and obscure detail by averaging the spectra. This approach does not improve signal to noise levels nor increase peak of interest amplitude. Spectral peaks are further obscured due to the lack of a sufficient number of fragment ions at any given collision energy level. It has now been discovered that summing the several mass spectra (for example, one per second) accumulated over the entire peak of interest elution interval and summing the daughter fragment ions obtained from each discrete collision energy generates a summary mass spectrum that dramatically increases spectral peak size while reducing the noise level. In other words, because a plurality of mass spectra fragmentation patterns can be obtained at that discrete level of collision energy, this procedure will cause the consistent peaks across substantially all of the mass spectra to sum and thus increase, while the noise in the system will tend to cancel across the mass spectra due to the more random nature of the noise.

The number of discrete collision energies used to sequence the peptide may vary depending on the nature of the peptide.

In one aspect for example, at least three discrete collision energies may be used. In another aspect, at least 5 discrete collision energies may be used. In yet another aspect, at least 7 discrete collision energies may be used. In a further aspect, at least 10 discrete collision energies may be used. Similarly, the discrete period of time used to collect mass spectra fragmentation data from a single discrete collision energy may vary depending on the nature of the peptide. The discrete period of time should be long enough to allow sufficient collection of data to facilitate accurate sequencing of the peptide, which in some aspects is the length of time that is required for a peak to elute. This is sometimes shortened if a potentially interfering peak eluates shortly before or after the peak of interest. In one specific aspect, for example, the discrete period of time may be approximately equal to the peptide's elution duration from the cLC or other separation process. In another specific aspect, the discrete period of time may be greater than or equal to the peptide's elution duration. In yet another aspect the discrete period of time may be less than the peptide's elution duration. In a further aspect specific aspect, the discrete period of time is from about 30 seconds to about 3 minutes.

Following creation of a discrete collision energy mass spectrum for each of the discrete collision energies, these summed mass spectra are then summed to form a final mass spectrum for the peptide. Summing the discrete collision energy mass spectra to form a final mass spectrum for the peptide adds the spectral peaks from each of the discrete collision energies into a single spectrum, thus forming an accurate mass spectral view of the peptide fragmentation pattern. As with the other summing operations described, this process functions to increase the signal to noise ratio of the mass spectra.

The final mass spectrum for the peptide can then be utilized to determine the amino acid sequence for the peptide. Any method for determining the sequence would be considered to be within the scope of the present invention. One method may include utilizing a protein database. One example of such a database in the MASCOT 'MS/MS Ion Search database. Discussion of the use of this database are included in the Examples below.

EXAMPLES

The following examples are provided to promote a more clear understanding of certain embodiments of the present invention, and are in no way meant as a limitation thereon.

Example 1

Serum Collection

The specimens used in the following examples were collected as part of a multi-center study carried out by the Maternal Fetal Medicine Units Network (MFMU). Samples were analyzed in an attempt to identify peptides that may be potential markers of spontaneous preterm delivery. Approximately 3000 pregnant women with singleton pregnancies were enrolled prior to 24 weeks gestation at 10 sites throughout the U.S., representing a racially and ethnically diverse population. The women studied were followed through delivery. Serum specimens were collected at 24 and 28 weeks gestation for measurement of selected specific proteins.

Approximately 400 of these specimens representing two groups (coded A and B) were collected for a proteomic study. The first of the two groups included mothers that experienced an uncomplicated term delivery while the second group included mothers that experienced a preterm delivery (<37 wks). Specimens from both the 24 week visit and 28 week visit were utilized. The samples were blinded as to pregnancy outcome and all other demographic or medical or obstetric data during the proteomic analysis.

Example 2

Acetonitrile Precipitation

Two volumes of HPLC grade acetonitrile (400 µL) were added to 200 µL of serum, vortexed vigorously for 5 sec and allowed to stand at room temperature for 30 min. Samples from Example 1 were then centrifuged for 10 min at 12,000 rpm in an IEC Micromax RF centrifuge (Thermo Fisher Scientific, Waltham, Mass.) at room temperature. An aliquot of supernatant (~550 µL) was then transferred to a microcentrifuge tube containing 300 µL HPLC grade water. The sample was vortexed briefly to mix the solution which was then lyophilized to ~200 µL in a Labconco CentriVap Concentrator (Labconco Corporation, Kansas City, Mo.). The volume of water added prior to lyophilization aids in the complete removal of acetonitrile from the solution. This is necessary because acetonitrile is incompatible with the assay used to determine protein concentration. Supernatant protein concentration were determined using a Bio-Rad microtiter plate protein assay performed according to manufacturer's instructions. An aliquot containing 4 µg of protein was transferred to a new microcentrifuge tube and lyophilized to near dryness. Samples were brought up to 20 µL with HPLC water and then acidified using 20 µL 88% formic acid.

Acetonitrile treated (post precipitation) serum samples (40 µL) were loaded into 250 µL conical polypropylene vials closed with polypropylene snap caps having septa (Dionex Corporation, Sunnyvale, Calif.), and placed into a FAMOS® autosampler 48 well plate kept at 4° C. The FAMOS® autosampler injected 5 µL of each serum sample onto a liquid chromatography guard column using HPLC water acidified with 0.1% formic acid at a flow rate of 40 µL/min. Detailed autosampler settings are shown in Table 1. Salts and other impurities were washed off of the guard column with the acidified water. Because the FAMOS® autosampler draws up three times the volume of what is loaded onto the column, it was necessary to inject the samples by hand when sample volume is limited. This was accomplished by injecting 10 µL volume of sample onto a blank loop upstream of the guard column and programming the FAMOS® autosampler to inject a 10 µL sample of HPLC water in place of the sample. The serum sample was loaded onto the guard column and desalted as if it had been loaded from the conical vials.

TABLE 1

| FAMOS ® Autosampler Settings | |
| --- | --- |
| Air Segment | No |
| Head Space Pressure | Yes |
| Tray Cooling | Yes |
| Tray Cooling Setpoint (° C.) | 4 |
| Needle Height (mm) | 5 |
| Syringe Size (µl) | 25 |
| Scale Factor | 0.2 |
| Syringe Speed | Normal |
| Loop Fill Mode | Partial |
| Loop Volume (µl) | 10 |
| Flush Volume (µl) | 5 |
| Analysis Time (sec) | 0 |
| Number of Injections | 1 |
| Injection Volume (µl) | 5 |

TABLE 1-continued

| FAMOS ® Autosampler Settings | |
| --- | --- |
| Low Dispersion Mode | No |
| Wash Volume (μL) | no |

Example 3

Liquid Chromatography Separation for Mass Spec Analysis

Capillary liquid chromatography (cCL) was performed to fractionate the samples obtained in Example 2. cLC used a 1 mm (16.2 μL) microbore guard column (Upchurch Scientific, Oak Harbor, Wash.) and a 15 cm×250 μm i.d. capillary column assembled in-house. The guard column was dry-packed and the capillary column was slurry packed using POROS R1 reversed-phase media (Applied Biosystems, Framingham, Mass.). Column equilibration and chromatographic separation were performed using an aqueous phase (98% HPLC grade $H_2O$, 2% acetonitrile, 0.1% formic acid) and an organic phase (2% HPLC $H_2O$, 98% acetonitrile, 0.1% formic acid). Separation was accomplished beginning with a 3 min column equilibration at 95% aqueous solution, followed by a 2.75%/min gradient increase to 60% organic phase, which was then increased at 7%/min to a concentration of 95% organic phase. The gradient was held at 95% organic phase for 7 min to elute the more hydrophobic components of the sample, and then the gradient was returned to 95% aqueous phase over 5 min and held at this concentration for 2 min to re-equilibrate the column. FIG. 1 shows such a cLC solvent gradient elution profile. All separations were performed at a flow rate of 5 μL/min. Chromatography used an LC Packings Ultimate Capillary HPLC pump system, with a FAMOS® autosampler (Dionex Corporation, Sunnyvale, Calif.), controlled by the Analyst QS® software supplied with the QSTAR® mass spectrometer (Applied Biosystems, Foster City, Calif.).

Example 4

MS Analysis

MS calibrations were performed daily prior to running samples, using the peptide [Glu$^1$]-fibrinopeptide B (Sigma, St. Louis, Mo.), a synthetic peptide not found endogenously. If needed, settings were adjusted to optimize signal to noise ratio and to maximize sensitivity.

The cLC system was coupled directly to a mass spectrometer. Effluent from the capillary column was directed into a QSTAR® Pulsar i quadrupole orthogonal time-of-flight mass spectrometer through an IonSpray source (Applied Biosystems). Data was collected for m/z 500 to 2500 beginning at 5 min and ending at 55 min. This delay in start time was programmed because, with a flow rate of 5 μl/min, it takes over 5 min for sample to get from the guard column to the mass spectrometer, and thus no useful data can be obtained before 5 min. Data collection, processing and preliminary formatting are accomplished using the Analyst QS® software package with BioAnalyst add-ons (Applied Biosystems). Specific instrument settings for MS analysis are shown in Table 2.

TABLE 2

| Mass Spectrometer Settings | |
| --- | --- |
| Scan Mode | None |
| Intensity Threshold | 1 counts |
| Settling Time | 0.000 ms |
| MR Pause | 5.007 ms |
| MCA | no |
| Ion Source Gas 1 (GS1) | 12.0-17.0 |
| Ion Source Gas 2 (GS2) | 0 |
| Curtain Gas (CUR) | 20.0 |
| IonSpray Voltage (IS) | 4800-5500 |
| Declustering Potential (DP) | 40.0-75.0 |
| Focusing Potential (FP) | 265.0-300.0 |
| Declustering Potential 2 (DP2) | 15.0 |
| Collision Gas (CAD) | 3.0-6.0 |
| Ion Release Delay (IRD) | 6.0 |
| Ion Release Width (IRW) | 5.0 |
| Focusing Rod Offset (Q0) | 20.0 |

Mass spectra were obtained every 1 sec throughout the entire cLC elution period for each specimen from both clinical groups A and B of Example 1. The elution profile of the cLC fractionated protein depleted serum of each subject, reported as the total ion chromatogram, was inspected to insure that it was consistent with previously run human sera. Specimens having an overall abundance less than 50% of normal or greater than 200% normal or lacking the characteristic series of three broad ion intense regions were rerun or omitted if there was inadequate specimen to redo the analysis.

Example 5

Peak Alignment

Figure 2A:
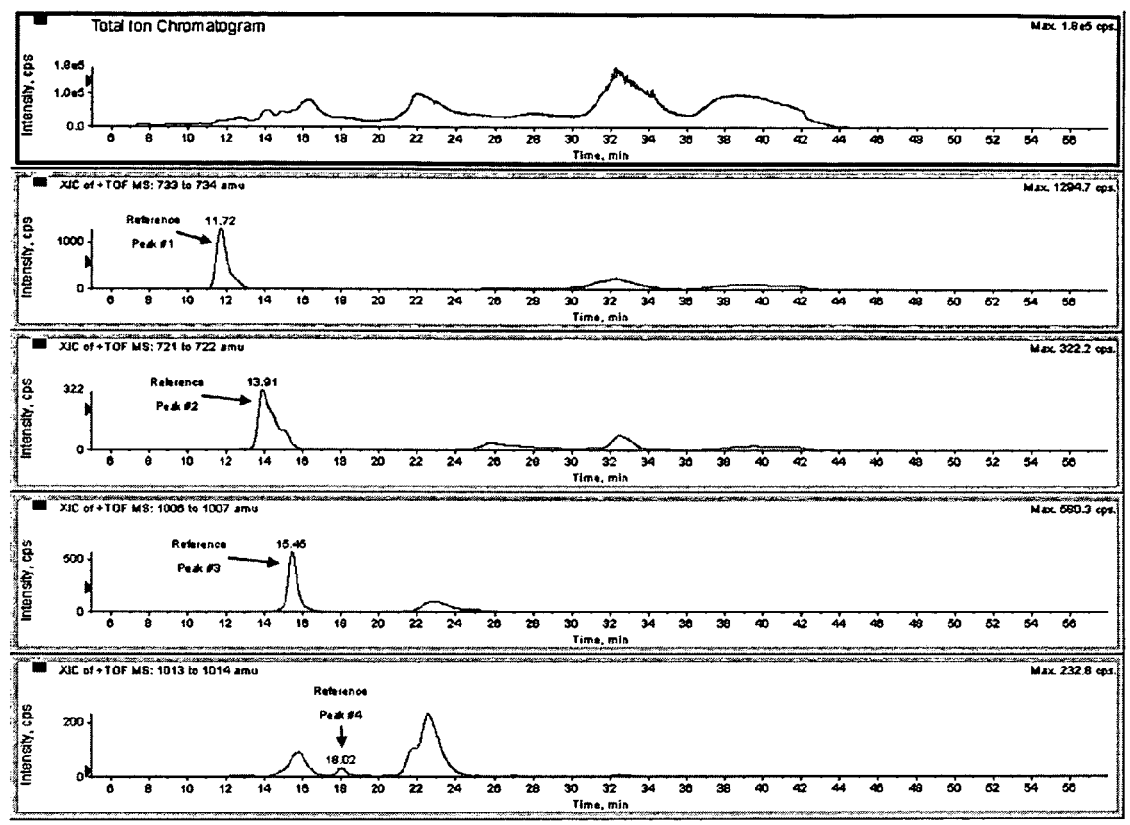
FIG. 2A is an elution profile of a series of molecular species used for chromatographic elution time alignment in accordance with another embodiment of the present invention.
Figure 2B:
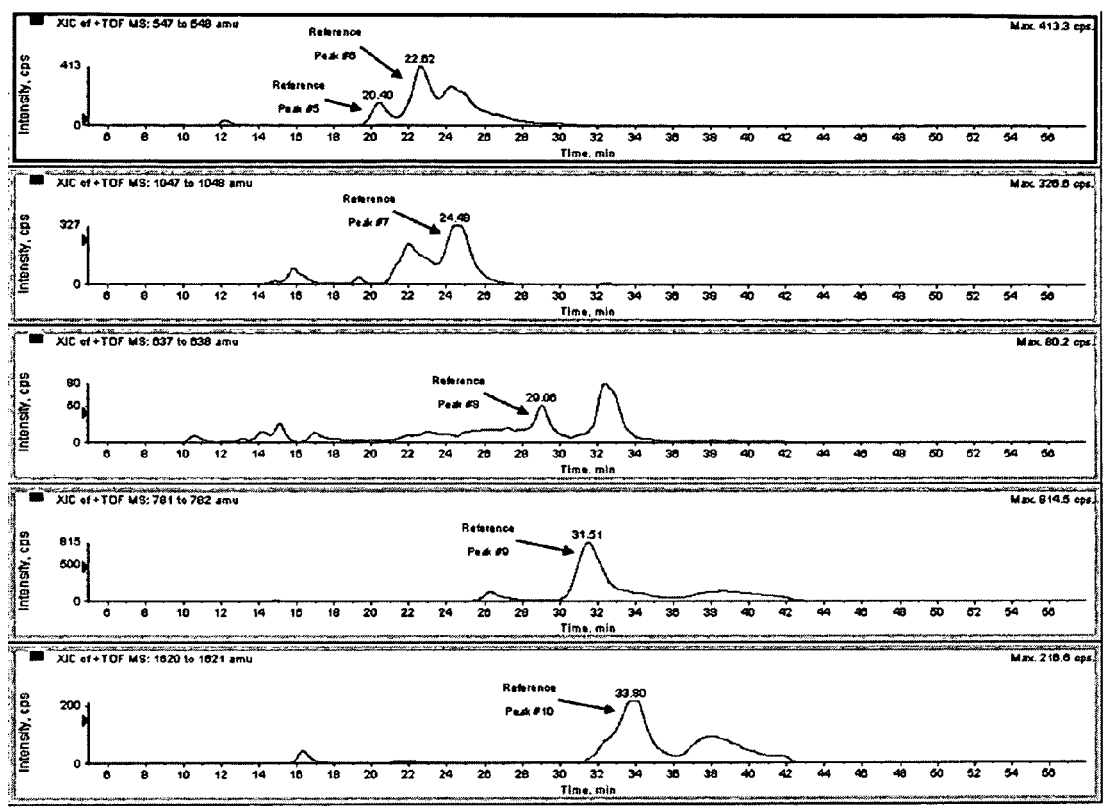
FIG. 2B is an elution profile of a series of molecular species used for chromatographic elution time alignment in accordance with another embodiment of the present invention.

Samples run on different days and on different columns can vary in elution times, and thus a peak alignment process was performed to equalize elution times. Ten endogenous molecular species of relatively high-abundance were found that elute at approximately 2 minute intervals throughout the most informative parts of the chromatogram. The Extract Ion Chromatogram (XIC) function was used to visualize the elution of the desired m/z ranges. The XIC ranges for each of the 10 endogenous molecular species are shown in Table 3. Additionally, FIGS. 2A and 2B show the elution profile of the individual molecular species used for chromatographic elution time alignment. The Gaussian Smooth function was used to smooth each XIC five times to insure the location of the center of the alignment reference peak apex to determine its exact elution time. This allowed all specimens to be aligned across elution times. Each of these alignment reference peak's elution times was then determined for each specimen run. Each of these elution times were then used as the center of a 2 min window by using the Set Selection function of the mass spectrometer. Then the Show Spectra function was used to create a single averaged mass spectrum from all the 1 sec mass spectra in that 2 min window. The software was then used to overlay spectra from the same 2 min elution interval from different specimens to visually inspect for differences between sample groups.

TABLE 3

| Endogenous Molecular Species XIC Range | |
| --- | --- |
| Peak Number | XIC Range |
| 1 | 733-734 |
| 2 | 721-722 |
| 3 | 1006-1007 |

TABLE 3-continued

Endogenous Molecular Species XIC Range

| Peak Number | XIC Range |
|---|---|
| 4 | 1013-1014 |
| 5 | 547-548 |
| 6 | 547-548 |
| 7 | 1047-1048 |
| 8 | 637-638 |
| 9 | 781-782 |
| 10 | 1620-1621 |

Example 6

Data Analysis

Analyst®, the software program supporting the Q-Star (q-TOF) mass spectrometer, allows for compilation of 16 individual liquid chromatographic runs and the comparison of mass spectra within those runs at similar elution times. Ten two-minute windows were established as described in Example 5 over the 20 min period of elution to allow data file size to remain manageable. The two minute windows were aligned as is also described in Example 5. Of the 10 two-minute elution intervals, the first to be analyzed was the second two-minute window, chosen because there were typically more peptide species present. Peptides were identified by the characteristic appearance of their multiply charged states which appear as a well defined cluster of peaks having a Gaussian shape with the individual peaks being separated by less than 1 mass/charge unit rather than a single peak or peaks separated by 1 mass/charge unit. Groups comprising 8 subjects from one group and 8 from another were color coded and overlaid. The data was then visually inspected and molecular species that seemed to be dominated by one color were recorded. This process was repeated for all additional sets of 8 cases and 8 controls. For a compound to be considered further, the same apparent difference between groups A and B was needed to be observed in at least two thirds of the data sets.

Molecules that appeared to be different between the two study groups were then individually inspected. These candidate species were all peptides. Prior to extracting quantitative data, the mass spectrum was examined to insure that the peptide peak had the same m/z and also represented the same charge state to further insure that the same peptide was being considered. Additionally, a second nearby peak, which did not demonstrate differences in abundance between the two groups, was selected as a reference. This peak was used to normalize the candidate peak of interest and correct for variability in specimen processing, specimen loading and ionization efficiencies.

The molecular species are then 'extracted' by the Analyst® software to determine the peak maxima of the individual molecular species in each individual run. This feature did not limit inspection of a specific m/z to a two minute elution window and consequently the peak used to align cLC elution time may be used additionally to insure the location in the elution profile was the same and hence insure that the same molecular species was selected each time.

The peak height for each molecular species was considered a reasonable estimate of its abundance. The abundance of each candidate compound was tabulated and the calculated value of each candidate species was ratioed to the nearby reference species. Because a single species was being considered, univariate statistical analysis was employed in evaluating possible differences in this peptide's abundance between the two groups.

Example 7

MS-MS and Amino Acid Sequence Analysis

MS-MS calibrations were performed daily prior to running of samples, using the peptide [Glu$^1$]-fibrinopeptide B (Sigma, St. Louis, Mo.), a synthetic peptide not found endogenously. If needed, settings were adjusted to optimize signal to noise ratio and to maximize sensitivity.

Previously run MS spectra as described in the examples above were inspected for peaks having high abundance of the candidate marker of interest. For those samples, frozen supernatant was thawed and the remaining volume of sample was measured. An aliquot of 88% formic acid equal to half the volume of the available sample was added, and the acidified sample was vortexed vigorously for 10 seconds to mix. All samples were hand injected for MS-MS analysis due to limited volume.

Figure 3:
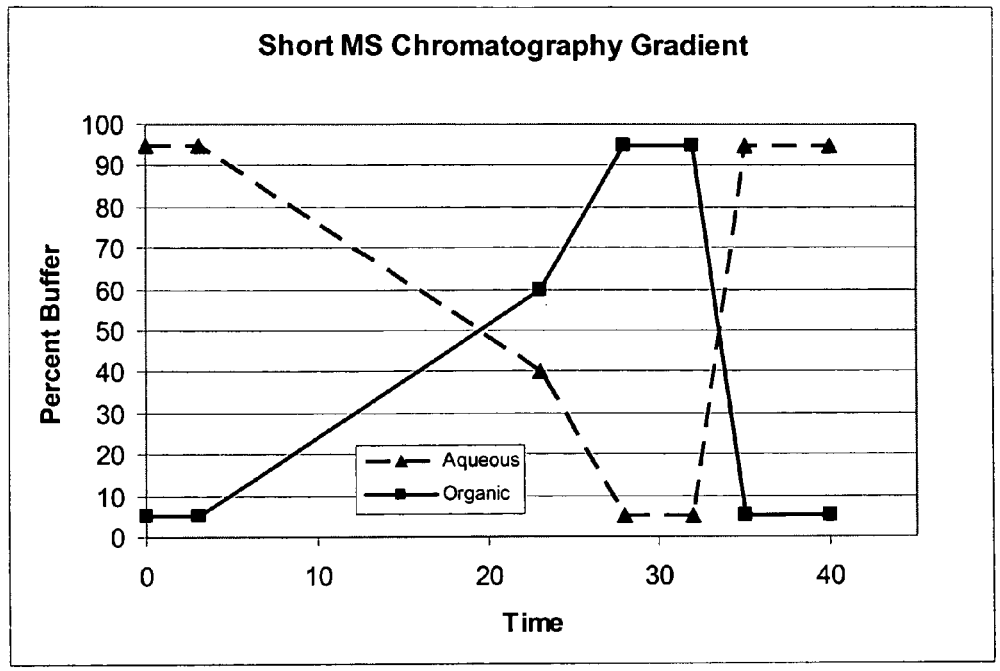
FIG. 3 is a capillary liquid chromatography solvent gradient elution profile in accordance with yet another embodiment of the present invention.

Capillary liquid chromatography (cLC) for MS-MS analysis was performed on the samples as is described in Example 3, with the following alterations: Because the peptides targeted for fragmentation eluted within the first half of the gradient, that portion of the program was not altered. However, for MS-MS analysis the time the gradient was held at 95% organic phase was shortened to 4 min, the gradient was returned to 95% aqueous phase in 3 min rather than 5 min and held at this concentration for a shortened time of 5 min to re-equilibrate the column. FIG. 3 shows such a cLC solvent gradient elution profile. All separations were performed using a flow rate of 5 µL/min.

A time-of flight (TOF)-MS-MS experiment was configured with a one second TOF-MS scan being taken for m/z of 500 to 2500, followed by a three second Positive Product Ion scan taken for the mass of interest. The selected ion was moved into a collision cell where it collided with an inert gas and fragmented at peptide bonds. The collision fragments were 'read' in a second MS.

A first targeted peptide (676.66 m/z) had a +3 charge corresponding to a neutral parent mass of 2026.98 Da. Second and third targeted peptides (856.85 m/z and 860.05 m/z) had +5 charges that correspond to neutral parent masses of 4279.25 Da and 4295.25 Da respectively. Setting the resolution of Q1 to 'LOW' allowed a small window of m/z values through the quadrupoles to be fragmented. For the +5 peaks, a good fragmentation was achieved by targeting a peak in the isotope window slightly above the monoisotopic peak. These TOF-MS-MS spectra were inspected for peak elution time and the collision energy used was optimized. The instrument settings are shown in Tables 4 and 5.

TABLE 4

MS Instrument Settings for cLC-TOF MS-MS Studies.

| TOF-MSMS Settings | |
|---|---|
| Scan Mode | None |
| Product of | 676.7, 857.2, or 860.2 amu |
| Resolution Q1 | LOW |
| Intensity Threshold | 0 counts |
| Settling Time | 0.000 ms |
| MR Pause | 5.007 ms |
| MCA | No |
| Ion Source Gas 1 (GS1) | 17.0 |

TABLE 4-continued

MS Instrument Settings for cLC-TOF MS-MS Studies.

TOF-MSMS Settings

| | |
|---|---|
| Ion Source Gas 2 (GS2) | 0.0 |
| Curtain Gas (CUR) | 17.0 |
| IonSpray Voltage (IS) | 4800.0 |
| Declustering Potential (DP) | 50.0 |
| Focusing Potential (FP) | 290.0 |
| Declustering Potential 2 (DP2) | 15.0 |
| Collision Energy (CE) | 30.0-40.0 |
| Collision Gas (CAD) | 12.0 |
| Ion Release Delay (IRD) | 6.0 |
| Ion Release Width (IRW) | 5.0 |

TABLE 5

MS instrumental settings when using the MCA function.

Positive Product Ion Settings

| | |
|---|---|
| Scan Mode | None |
| Product of | 676.7, 857.2, or 860.2 amu |
| Resolution Q1 | LOW |
| Intensity Threshold | 0 counts |
| Settling Time | 0.000 ms |
| MR Pause | 5.007 ms |
| MCA | Yes |
| Ion Source Gas 1 (GS1) | 17.0 |
| Ion Source Gas 2 (GS2) | 0.0 |
| Curtain Gas (CUR) | 17.0 |
| IonSpray Voltage (IS) | 4800 |
| Declustering Potential (DP) | 50.0 |
| Focusing Potential (FP) | 290.0 |
| Declustering Potential 2 (DP2) | 15.0 |
| Collision Energy (CE) | 27-45 |
| Collision Gas (CAD) | 12.0 |
| Ion Release Delay (IRD) | 6.0 |
| Ion Release Width (IRW) | 5.0 |

Example 8

Peak m/z 676.66

Peak m/z 676.7 described in Example 7 eluted from 12.7 to 13.7 min from the cLC system. Species with different elution times and charge states were observed that had peaks in the same m/z range of the peak of interest. To avoid fragmenting these other species, MS-MS fragmentation data was collected for m/z 70 to 2000 beginning at 12.7 minutes and ending at 13.7 minutes. One spectrum was taken every second, so this one min window collected 60 spectra. The MCA function allowed for the summation of all 60 MS-MS spectra as they are taken. These summed spectra provided greatly increased signal and reduced noise. Because rolling collision energy cannot be used with the MCA feature, 0.5 µg of sample were run four times with collision energies set at 27, 30, 35, and 40. Using different collision energies allowed a better sequence coverage in the fragmentation patterns. The Add Data feature was used to sum these four MCA spectra together, resulting in a single MS-MS spectrum with good fragmentation coverage over much of the sequence of the peptide. The threshold of this spectrum was manually set to 1.5 and the data was centroided. After the centroided data threshold was set to 3.0, the data list was exported to Excel®. The spectrum was visually inspected and compared to the exported data list to make sure the software had assigned charge states correctly. After correction, the data list was transformed using Formula (I) so that all species had a +1 mass:

$$+1 \text{ mass} = m/z \text{ value} \cdot \text{charge} - (\text{charge} - 1) \qquad (I)$$

Peaks with undefined charges were left as originally exported. This corrected list was appended to the non-corrected mass list, and the mass list with corresponding intensities was exported as a tab-delimited text file submitted to Mascot. Mascot (www.matrixscience.com) is a searchable MS database meant to allow protein/peptide identification. Mascot only matches +1 and +2 fragments, so converting all species to +1 allowed Mascot to match peptides that have a charge at or above +3. The text file was edited to have the following format:
SEARCH=MIS
REPTYPE=Peptide
BEGIN IONS
PEPMASS=676.6
tab delimited data list (m/z intensity)
END IONS
This text file was saved as a .tmp file and submitted to a MASCOT 'MS/MS Ions Search.' The NCBInr database was searched, limiting the searching to mammalian sequences. Under the enzyme setting, 'none' was chosen, with peptide and MS/MS tolerances of ±0.8 Da, with a +3 peptide charge selected. The data was in Mascot generic format, and the instrument used was a ESI-QUAD-TOF. The results of this submission are provided in Table 6.

TABLE 6

| # | B | $b^{++}$ | $b^*$ | $b^{*++}$ | $b^0$ | $b^{0++}$ | Seq. | y | $y^{++}$ | $y^0$ | $y^{0++}$ | # |
|---|---|---|---|---|---|---|---|---|---|---|---|---|
| 1 | 129.0659 | 65.0366 | 112.0393 | 56.5233 | | | Q | | | | | 19 |
| 2 | 242.1499 | 121.5786 | 225.1234 | 113.0653 | | | L | 1899.9388 | 950.4730 | 1881.9282 | 941.4677 | 18 |
| 3 | 299.1714 | 150.0893 | 282.1448 | 141.5761 | | | G | 1786.8547 | 893.9310 | 1768.8441 | 884.9257 | 17 |
| 4 | 412.2554 | 206.6314 | 395.2289 | 198.1181 | | | L | 1729.8332 | 865.4203 | 1711.8227 | 856.4150 | 16 |
| 5 | 509.3082 | 255.1577 | 492.2816 | 246.6445 | | | P | 1616.7492 | 808.8782 | 1598.7386 | 799.8729 | 15 |
| 6 | 566.3297 | 283.6685 | 549.3031 | 275.1552 | | | G | 1519.6964 | 760.3518 | 1501.6858 | 751.3466 | 14 |
| 7 | 663.3824 | 332.1948 | 646.3559 | 323.6816 | | | P | 1462.6750 | 731.8411 | 1444.6644 | 722.8358 | 13 |
| 8 | 760.4352 | 380.7212 | 743.4086 | 372.2080 | | | P | 1365.6222 | 683.3147 | 1347.6116 | 674.3095 | 12 |
| 9 | 875.4621 | 438.2347 | 858.4356 | 429.7214 | 857.4516 | 429.2294 | D | 1268.5694 | 634.7884 | 1250.5589 | 625.7831 | 11 |
| 10 | 974.5305 | 487.7689 | 957.5040 | 479.2556 | 956.5200 | 478.7636 | V | 1153.5425 | 577.2749 | 1135.5319 | 568.2696 | 10 |
| 11 | 1071.5833 | 536.2953 | 1054.5567 | 527.7820 | 1053.5727 | 527.2900 | P | 1054.4741 | 527.7407 | 1036.4635 | 518.7354 | 9 |
| 12 | 1186.6102 | 593.8088 | 1169.5837 | 585.2955 | 1168.5997 | 584.8035 | D | 957.4213 | 479.2143 | 939.4108 | 470.2090 | 8 |
| 13 | 1323.6691 | 662.3382 | 1306.6426 | 653.8249 | 1305.6586 | 653.3329 | H | 842.3944 | 421.7008 | | | 7 |
| 14 | 1394.7062 | 697.8568 | 1377.6797 | 689.3435 | 1376.6957 | 688.8515 | A | 705.3355 | 353.1714 | | | 6 |
| 15 | 1465.7434 | 733.3753 | 1448.7168 | 724.8620 | 1447.7328 | 724.3700 | A | 634.2984 | 317.6528 | | | 5 |
| 16 | 1628.8067 | 814.9070 | 1611.7801 | 806.3937 | 1610.7961 | 805.9017 | Y | 563.2613 | 282.1343 | | | 4 |

TABLE 6-continued

| # | B | b++ | b* | b*++ | b⁰ | b⁰++ | Seq. | y | y++ | y⁰ | y⁰++ | # |
|---|---|---|---|---|---|---|---|---|---|---|---|---|
| 17 | 1765.8656 | 883.4364 | 1748.8390 | 874.9232 | 1747.8550 | 874.4312 | H | 400.1979 | 200.6026 | | | 3 |
| 18 | 1862.9184 | 931.9628 | 1845.8918 | 923.4495 | 1844.9078 | 922.9575 | P | 263.1390 | 132.0731 | | | 2 |
| 19 | | | | | | | F | 166.0863 | 83.5468 | | | 1 |

Monoisotopic mass of neutral peptide Mr(calc): 2026.9901
Ions Score: 52 Expect: 0.86
Matches (Bold): 50/150 fragment ions using 156 most intense peaks Peaks in bold are matched to the sequence identified. The peptide sequence (using standard single letter amino acid identifiers) is 'qlglpgppdvpdhaayhpf' (SEQ ID NO 1).

Example 9

Peak m/z 856.8

Peak m/z 856.8 described in Example 7 eluted within a one minute time window, just as did peak m/z 676.6. Other species were not observed in the same m/z range of peak m/z 856.8, and therefore a larger time window could be used to collect fragmentation data. A 1.5 minute window started at collision energy (CE) 40 was used, followed by a 2 minute window for CE 38, CE 42, and CE 45. MS-MS fragmentation data was collected for m/z 70 to 2000 as described in Example 8. Due to limited sample volumes, however, only 0.4 µg was used at CE 38, but 0.5 µg was used for CE 40, CE 42 and CE 45. The 'Add Data' feature was employed to add these four MCA spectra together, giving a single MS-MS spectrum with good fragmentation coverage over much of the peptide sequence. The spectra were smoothed once and then the threshold of this spectrum was manually set to 2.0 and the data centroided. After setting the centroided data threshold to 3.0, the data list was exported to Excel®. The spectrum was visually inspected and compared to the exported data list to make sure the software had assigned charge states correctly. After correction, the data list was converted manually using Formula (I) so that all species had a +1 mass listed. Peaks with undefined charges were left as originally exported. This corrected list was appended to the non-corrected mass list, and the mass list with corresponding intensities was exported as a tab-delimited text file. The text file is edited to have the following format:
SEARCH=MIS
REPTYPE=Peptide
BEGIN IONS
PEPMASS=856.8
tab delimited data list (m/z intensity)
END IONS
This text file was saved as a .tmp file and submitted to a MASCOT 'MS/MS Ions Search' using the same settings as described in Example 8. The results of the submission are shown in Table 7.

TABLE 7

| # | b | b++ | b* | b*++ | b⁰ | b⁰++ | Seq. |
|---|---|---|---|---|---|---|---|
| 1 | 115.0502 | 58.0287 | 98.0237 | 49.5155 | | | N |
| 2 | 214.1186 | 107.5629 | 197.0921 | 99.0497 | | | V |
| 3 | 351.1775 | 176.0924 | 334.1510 | 167.5791 | | | H |
| 4 | 438.2096 | 219.6084 | 421.1830 | 211.0951 | 420.1990 | 210.6031 | S |
| 5 | 509.2467 | 255.1270 | 492.2201 | 246.6137 | 491.2361 | 246.1217 | A |
| 6 | 566.2681 | 283.6377 | 549.2416 | 275.1244 | 548.2576 | 274.6324 | G |
| 7 | 637.3052 | 319.1563 | 620.2787 | 310.6430 | 619.2947 | 310.1510 | A |
| 8 | 708.3423 | 354.6748 | 691.3158 | 346.1615 | 690.3318 | 345.6695 | A |
| 9 | 765.3638 | 383.1855 | 748.3373 | 374.6723 | 747.3532 | 374.1803 | G |
| 10 | 852.3958 | 426.7016 | 835.3693 | 418.1883 | 834.3853 | 417.6963 | S |
| 11 | 1008.4969 | 504.7521 | 991.4704 | 496.2388 | 990.4864 | 495.7468 | R |
| 12 | 1139.5374 | 570.2724 | 1122.5109 | 561.7591 | 1121.5269 | 561.2671 | M |
| 13 | 1253.5804 | 627.2938 | 1236.5538 | 618.7805 | 1235.5698 | 618.2885 | N |
| 14 | 1400.6488 | 700.8280 | 1383.6222 | 692.3147 | 1382.6382 | 691.8227 | F |
| 15 | 1556.7499 | 778.8786 | 1539.7233 | 770.3653 | 1538.7393 | 769.8733 | R |
| 16 | 1653.8026 | 827.4050 | 1636.7761 | 818.8917 | 1635.7921 | 818.3997 | P |
| 17 | 1710.8241 | 855.9157 | 1693.7975 | 847.4024 | 1692.8135 | 846.9104 | G |
| 18 | 1809.8925 | 905.4499 | 1792.8660 | 896.9366 | 1791.8819 | 896.4446 | V |
| 19 | 1922.9766 | 961.9919 | 1905.9500 | 953.4786 | 1904.9660 | 952.9866 | L |
| 20 | 2010.0086 | 1005.5079 | 1992.9820 | 996.9947 | 1991.9980 | 996.5027 | S |
| 21 | 2097.0406 | 1049.0240 | 2080.0141 | 1040.5107 | 2079.0301 | 1040.0187 | S |
| 22 | 2253.1417 | 1127.0745 | 2236.1152 | 1118.5612 | 2235.1312 | 1118.0692 | R |
| 23 | 2381.2003 | 1191.1038 | 2364.1738 | 1182.5905 | 2363.1898 | 1182.0985 | Q |
| 24 | 2494.2844 | 1247.6458 | 2477.2578 | 1239.1326 | 2476.2738 | 1238.6405 | L |
| 25 | 2551.3058 | 1276.1566 | 2534.2793 | 1267.6433 | 2533.2953 | 1267.1513 | G |
| 26 | 2664.3899 | 1332.6986 | 2647.3633 | 1324.1853 | 2646.3793 | 1323.6933 | L |
| 27 | 2761.4427 | 1381.2250 | 2744.4161 | 1372.7117 | 2743.4321 | 1372.2197 | P |
| 28 | 2818.4641 | 1409.7357 | 2801.4376 | 1401.2224 | 2800.4536 | 1400.7304 | G |
| 29 | 2915.5169 | 1458.2621 | 2898.4903 | 1449.7488 | 2897.5063 | 1449.2568 | P |
| 30 | 3012.5696 | 1506.7885 | 2995.5431 | 1498.2752 | 2994.5591 | 1497.7832 | P |
| 31 | 3127.5966 | 1564.3019 | 3110.5700 | 1555.7887 | 3109.5860 | 1555.2966 | D |
| 32 | 3226.6650 | 1613.8361 | 3209.6384 | 1605.3229 | 3208.6544 | 1604.8308 | V |
| 33 | 3323.7177 | 1662.3625 | 3306.6912 | 1653.8492 | 3305.7072 | 1653.3572 | P |
| 34 | 3438.7447 | 1719.8760 | 3421.7181 | 1711.3627 | 3420.7341 | 1710.8707 | D |
| 35 | 3575.8036 | 1788.4054 | 3558.7770 | 1779.8922 | 3557.7930 | 1779.4002 | H |
| 36 | 3646.8407 | 1823.9240 | 3629.8142 | 1815.4107 | 3628.8301 | 1814.9187 | A |

TABLE 7-continued

| | | | | | | | |
|---|---|---|---|---|---|---|---|
| 37 | 3717.8778 | 1859.4425 | 3700.8513 | 1850.9293 | 3699.8673 | 1850.4373 | A |
| 38 | 3880.9411 | 1940.9742 | 3863.9146 | 1932.4609 | 3862.9306 | 1931.9689 | Y |
| 39 | 4018.0001 | 2009.5037 | 4000.9735 | 2000.9904 | 3999.9895 | 2000.4984 | H |
| 40 | 4115.0528 | 2058.0300 | 4098.0263 | 2049.5168 | 4097.0423 | 2049.0248 | P |
| 41 | | | | | | | F |

| Seq. | y | y$^{++}$ | y* | y*$^{++}$ | y$^0$ | y$^{0++}$ | # |
|---|---|---|---|---|---|---|---|
| N | | | | | | | 41 |
| V | 4166.0889 | 2083.5481 | 4149.0623 | 2075.0348 | 4148.0783 | 2074.5428 | 40 |
| H | 4067.0205 | 2034.0139 | 4049.9939 | 2025.5006 | 4049.0099 | 2025.0086 | 39 |
| S | 3929.9615 | 1965.4844 | 3912.9350 | 1956.9711 | 3911.9510 | 1956.4791 | 38 |
| A | 3842.9295 | 1921.9684 | 3825.9030 | 1913.4551 | 3824.9189 | 1912.9631 | 37 |
| G | 3771.8924 | 1886.4498 | 3754.8659 | 1877.9366 | 3753.8818 | 1877.4446 | 36 |
| A | 3714.8709 | 1857.9391 | 3697.8444 | 1849.4258 | 3696.8604 | 1848.9338 | 35 |
| A | 3643.8338 | 1822.4206 | 3626.8073 | 1813.9073 | 3625.8233 | 1813.4153 | 34 |
| G | 3572.7967 | 1786.9020 | 3555.7702 | 1778.3887 | 3554.7862 | 1777.8967 | 33 |
| S | 3515.7753 | 1758.3913 | 3498.7487 | 1749.8780 | 3497.7647 | 1749.3860 | 32 |
| R | 3428.7432 | 1714.8753 | 3411.7167 | 1706.3620 | 3410.7327 | 1705.8700 | 31 |
| M | 3272.6421 | 1636.8247 | 3255.6156 | 1628.3114 | 3254.6316 | 1627.8194 | 30 |
| N | 3141.6016 | 1571.3045 | 3124.5751 | 1562.7912 | 3123.5911 | 1562.2992 | 29 |
| F | 3027.5587 | 1514.2830 | 3010.5322 | 1505.7697 | 3009.5481 | 1505.2777 | 28 |
| R | 2880.4903 | 1440.7488 | 2863.4638 | 1432.2355 | 2862.4797 | 1431.7435 | 27 |
| P | 2724.3892 | 1362.6982 | 2707.3626 | 1354.1850 | 2706.3786 | 1353.6930 | 26 |
| G | 2627.3364 | 1314.1719 | 2610.3099 | 1305.6586 | 2609.3259 | 1305.1666 | 25 |
| V | 2570.3150 | 1285.6611 | 2553.2884 | 1277.1478 | 2552.3044 | 1276.6558 | 24 |
| L | 2471.2466 | 1236.1269 | 2454.2200 | 1227.6136 | 2453.2360 | 1227.1216 | 23 |
| S | 2358.1625 | 1179.5849 | 2341.1360 | 1171.0716 | 2340.1519 | 1170.5796 | 22 |
| S | 2271.1305 | 1136.0689 | 2254.1039 | 1127.5556 | 2253.1199 | 1127.0636 | 21 |
| R | 2184.0984 | 1092.5529 | 2167.0719 | 1084.0396 | 2166.0879 | 1083.5476 | 20 |
| Q | 2027.9973 | 1014.5023 | 2010.9708 | 1005.9890 | 2009.9868 | 1005.4970 | 19 |
| L | 1899.9388 | 950.4730 | | | 1881.9282 | 941.4677 | 18 |
| G | 1786.8547 | 893.9310 | | | 1768.8441 | 884.9257 | 17 |
| L | 1729.8332 | 865.4203 | | | 1711.8227 | 856.4150 | 16 |
| P | 1616.7492 | 808.8782 | | | 1598.7386 | 799.8729 | 15 |
| G | 1519.6964 | 760.3518 | | | 1501.6858 | 751.3466 | 14 |
| P | 1462.6750 | 731.8411 | | | 1444.6644 | 722.8358 | 13 |
| P | 1365.6222 | 683.3147 | | | 1347.6116 | 674.3095 | 12 |
| D | 1268.5694 | 634.7884 | | | 1250.5589 | 625.7831 | 11 |
| V | 1153.5425 | 577.2749 | | | 1135.5319 | 568.2696 | 10 |
| P | 1054.4741 | 527.7407 | | | 1036.4635 | 518.7354 | 9 |
| D | 957.4213 | 479.2143 | | | 939.4108 | 470.2090 | 8 |
| H | 842.3944 | 421.7008 | | | | | 7 |
| A | 705.3355 | 353.1714 | | | | | 6 |
| A | 634.2984 | 317.6528 | | | | | 5 |
| Y | 563.2613 | 282.1343 | | | | | 4 |
| H | 400.1979 | 200.6026 | | | | | 3 |
| P | 263.1390 | 132.0731 | | | | | 2 |
| F | 166.0863 | 83.5468 | | | | | 1 |

Monoisotopic mass of neutral peptide Mr(calc): 4279.1245
Ions Score: 0 Expect: 3.8e+04
Matches (Bold): 47/424 fragment ions using 274 most intense peaks Peaks in bold represent matches to the peptide sequence. The amino acid sequence of this peptide is 'nvhsagaagsrmnfrpgvlssrqlglpgppdvpdhaayhpf' (SEQ ID NO 2).

Example 10

Peak m/z 860.0

Figure 4:
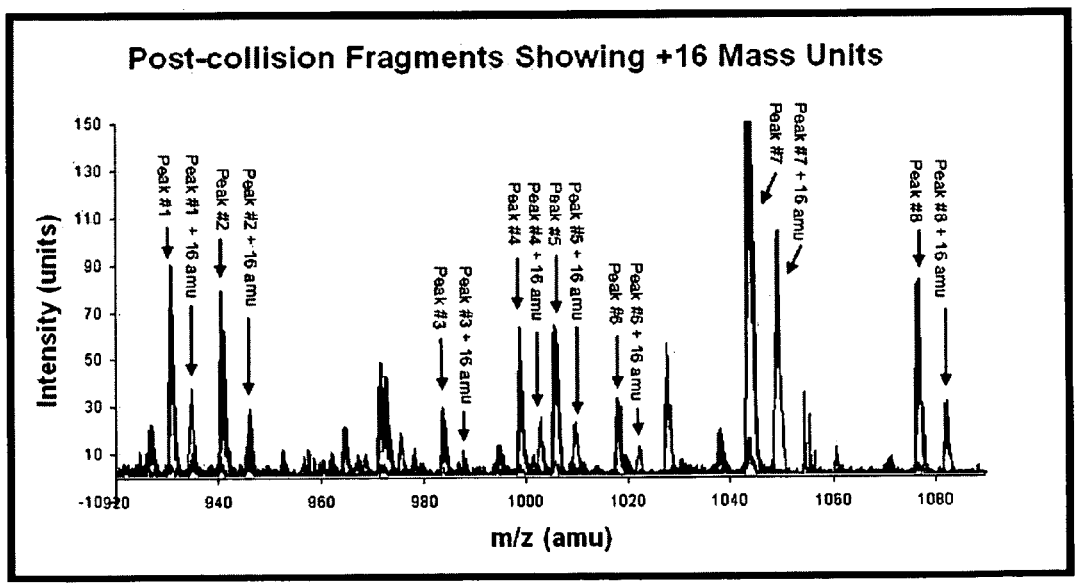
FIG. 4 is a graphical plot of mass spectra fragmentation patterns in accordance with a further embodiment of the present invention.
Figure 5:
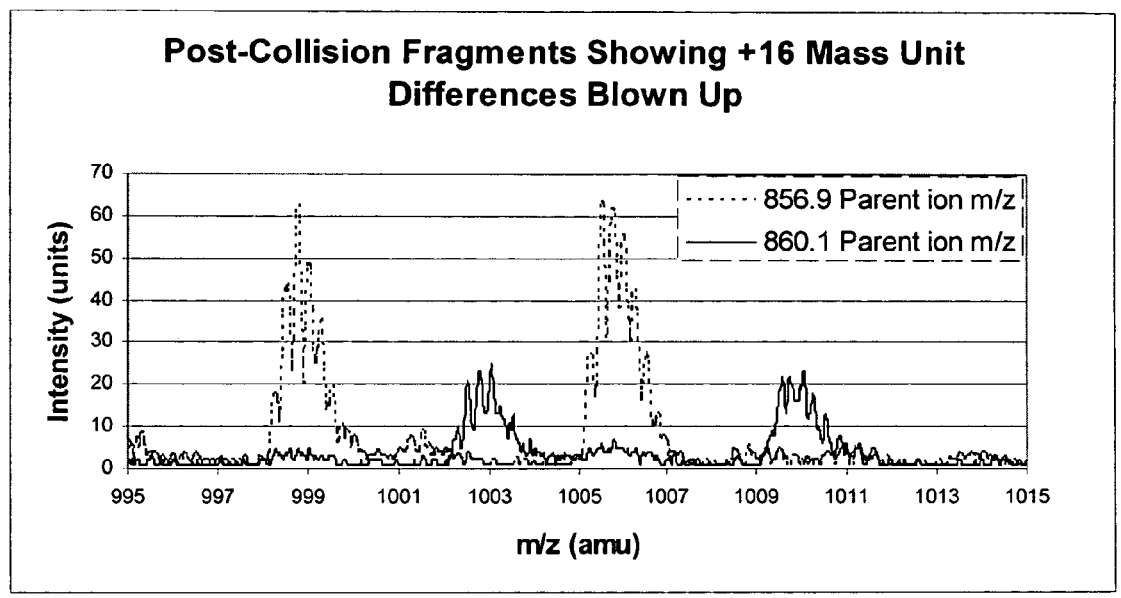
FIG. 5 is a graphical plot of mass spectra fragmentation patterns in accordance with yet a further embodiment of the present invention.

Peak m/z 860.0 described in Example 7 eluted within a one min time window. Because other species were not observed in the same m/z range as this peak of interest, a larger time window could be used to collect fragmentation data. A 2 min window started at CE 40 was used, followed by a 3 min window for CE 38, CE 42, and CE 45. MS-MS fragmentation data was collected for m/z 70 to 2000 as in Examples 8 and 9. Due to limited sample volumes, only 0.25 µg of protein for each of the four runs was loaded to perform fragment studies of this species. The 'Add Data' feature was used to sum these four MCA spectra together, resulting in a single MSMS spectrum with good fragmentation coverage over much of the sequence of the peptide. Because fragmentation of this species looked similar to that of m/z 856.7, the two spectra were overlaid and a +16 m/z mass shift was observed for many fragments, as is shown in FIGS. 4 and 5. The broken-line peaks in FIG. 5 are fragmentation peaks from m/z 857.8 and the solid-line peaks are from m/z 860.0. All of the peaks that show a 16 m/z shift are those on the C-Terminal side of the one methionine in the sequence, while all of the peaks that do not show a shift are those on the N-Terminal side of the methionine. This suggests strongly that the molecular species m/z 860.0 is oxidized at its methionine, but is otherwise identical in amino acid sequence to peak m/z 857.8. Thus the amino acid sequence of this peptide is 'nvhsagaagsrm$^{(O)}$nfrpgvlssrqlglpgppdvpdhaayhpf' (SEQ ID NO 3), where m$^{(O)}$ represents an oxidized methionine.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for comparing multiple mass spectra from different biological samples, locating mass ions that are quantitatively different after using approaches to compensate for non-biological variability, and isolating and sequencing at least one peptide of interest thus allowing for identification of the peptide from a biological sample, comprising:
    fractionating each of a plurality of biological samples to form a plurality of elutions;
    obtaining a plurality of mass spectra from each of the plurality of elutions at a plurality of elution times;
    finding a molecular ion peak of interest that appears to be quantitatively different between biological samples;
    identifying a mass spectrum reference peak corresponding to an endogenous reference molecule that is substantially consistent between biological samples, the endogenous reference molecule having an elution time and a mass to charge ratio that are substantially similar to the peak of interest;
    compensating for non-biological variation for each biological sample across the plurality of elutions by normalizing the peak of interest to a mass spectrum peak of the endogenous reference molecule; and
    fractionating at least one of the biological samples containing the peptide associated with the peak of interest to at least partially isolate the peptide;
    obtaining mass spectra of the peptide;
    accelerating the peptide into a collision chamber at a plurality of discrete collision energies for a discrete period of time to form a plurality of peptide fragments for each of the plurality of discrete collision energies;
    obtaining a plurality of fragmentation mass spectra from the plurality of peptide fragments for each of the plurality of discrete collision energies;
    summing the plurality of fragmentation mass spectra from each of the plurality of discrete collision energies to form a plurality of discrete collision energy mass spectra, one discrete collision energy mass spectra from each discrete collision energy;
    summing the plurality of discrete collision energy mass spectra to form a final mass spectrum for the peptide fragments; and
    identifying a sequence of amino acids corresponding to the peptide from the final mass spectrum.

2. The method of claim 1, wherein the biological samples are blood serum samples.

3. The method of claim 1, further comprising:
    identifying a plurality of mass spectrum elution time alignment peaks in the plurality of mass spectra corresponding to a plurality of endogenous alignment molecules such that each of the plurality of elutions contains at least one mass spectrum elution time alignment peak; and
    aligning at least a portion of the plurality of mass spectra by aligning at least a portion of the plurality of mass spectrum elution time alignment peaks.

4. The method of claim 3, wherein aligning the pluralities of mass spectra further includes visually aligning the pluralities of mass spectra using the mass spectrum alignment peak as a reference.

5. The method of claim 1, wherein the endogenous alignment molecules have a substantially uniform abundance in each of the plurality of biological samples.

6. The method of claim 1, wherein fractionating each of the plurality of biological samples further includes fractionating each of the biological samples by capillary liquid chromatography.

7. The method of claim 1, wherein the discrete period of time is approximately equal to the peptide's elution duration.

8. The method of claim 6, wherein the discrete period of time is greater than or equal to the peptide's elution duration.

9. The method of claim 1, wherein the discrete period of time is less than the peptide's elution duration.

10. The method of claim 1, wherein the discrete period of time is from about 30 seconds to about 3 minutes.

11. The method of claim 10, wherein the endogenous reference molecule has a substantially representative abundance in each of the plurality of biological samples.

12. A method of sequencing a peptide, comprising:
    fractionating a biological sample containing a peptide of interest to at least partially isolate the peptide;
    obtaining mass spectra of the peptide;
    accelerating the peptide into a collision chamber at a plurality of discrete collision energies for a discrete period of time to form a plurality of peptide fragments for each of the plurality of discrete collision energies;
    obtaining a plurality of fragmentation mass spectra from the plurality of peptide fragments for each of the plurality of discrete collision energies;
    summing the plurality of fragmentation mass spectra from each of the plurality of discrete collision energies to form a plurality of discrete collision energy mass spectra, one discrete collision energy mass spectra from each discrete collision energy;
    summing the plurality of discrete collision energy mass spectra to form a final mass spectrum for the peptide fragments; and
    identifying a sequence of amino acids corresponding to the peptide of interest from the final mass spectrum.

13. The method of claim 12, wherein the discrete period of time is approximately equal to the peptide's elution duration.

14. The method of claim 12, wherein the discrete period of time is greater than or equal to the peptide's elution duration.

15. The method of claim 12, wherein the discrete period of time is from about 30 seconds to about 3 minutes.

16. The method of claim 12, wherein the plurality of discrete collision energies is at least 3 discrete collision energies.

17. The method of claim 12, wherein the plurality of discrete collision energies is at least 5 discrete collision energies.

18. The method of claim 12, wherein the plurality of discrete collision energies is at least 7 discrete collision energies.

* * * * *